US00PP19784P2

(12) United States Plant Patent
Danziger

(10) Patent No.: US PP19,784 P2
(45) Date of Patent: Mar. 3, 2009

(54) ***NEMESIA* PLANT NAMED 'DANNEMES4'**

(50) Latin Name: *Nemesia fruticans*
Varietal Denomination: Dannemes4

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,643

(22) Filed: Jan. 11, 2008

(51) Int. Cl.
*A01H 5/00* (2006.01)

(52) U.S. Cl. ..... Plt./458

(58) Field of Classification Search ..... Plt./458, Plt./263

See application file for complete search history.

*Primary Examiner*—Annette H Para
*Assistant Examiner*—S. B. McCormick Ewoldt

(57) ABSTRACT

A new and distinct *Nemesia* cultivar named 'Dannemes4' is disclosed, characterized by having clear white flowers flowers, upright plant habit, early flowering, and a high temperature tolerance. The new variety is a *Nemesia,* normally produced as an outdoor garden or container plant.

2 Drawing Sheets

Latin name of the genus and species: *Nemesia fruticans.* Variety denomination: 'Dannemes4'.

BACKGROUND OF THE INVENTION

The new *Nemesia* cultivar is a product of a planned breeding program conducted by the inventor, Gabriel Danziger, in Moshav Mishmar Hashiva, Israel. The objective of the breeding program was to produce new varieties of *Nemesia* for commercial introduction. The seed parent is the unpatented, proprietary seedling variety referred to as *Nemesia fruticans* 'NE-Z-21.' The pollen parent is unknown as the new variety is the result of an open pollination in which the male parent cannot be identified. The new variety was discovered in April 2006 by the inventor in a group of seedlings resulting from that crossing, in a commercial greenhouse in Moshav Mishmar Hashiva, Israel. Asexual reproduction of the new cultivar 'Dannemes4' by vegetative cuttings was first performed at a commercial greenhouse in Moshav Mishmar Hashiva, Israel in September 2006. Subsequent propagation has shown that the unique features of this cultivar are stable and reproduced true to type on successive generations.

SUMMARY OF THE INVENTION

The cultivar 'Dannemes4' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Dannemes4' These characteristics in combination distinguish 'Dannemes4' as a new and distinct *Nemesia* cultivar:

1. Vigor.
2. Pure white flower color.
3. Early flowering.
4. High temperature tolerance.

Plants of the new cultivar 'Dannemes4' are similar to plants of the parent, *Nemesia fruticans* 'NE-Z-21' in most horticultural characteristics, however, plants of the new cultivar 'Dannemes4' have a different color flower.

Commercial Comparison

Plants of the new cultivar 'Dannemes4' are best compared to the commercial variety 'Balarwite,' U.S. Plant Pat. No. 17,592. Plants of 'Dannemes4' are similar to plants of 'Balarwite' in most horticultural characteristics, however, plants of the new variety are taller and flower earlier than plants of 'Balarwite.'

BRIEF DESCRIPTION OF THE PHOTOGRAPH

Figure 1:
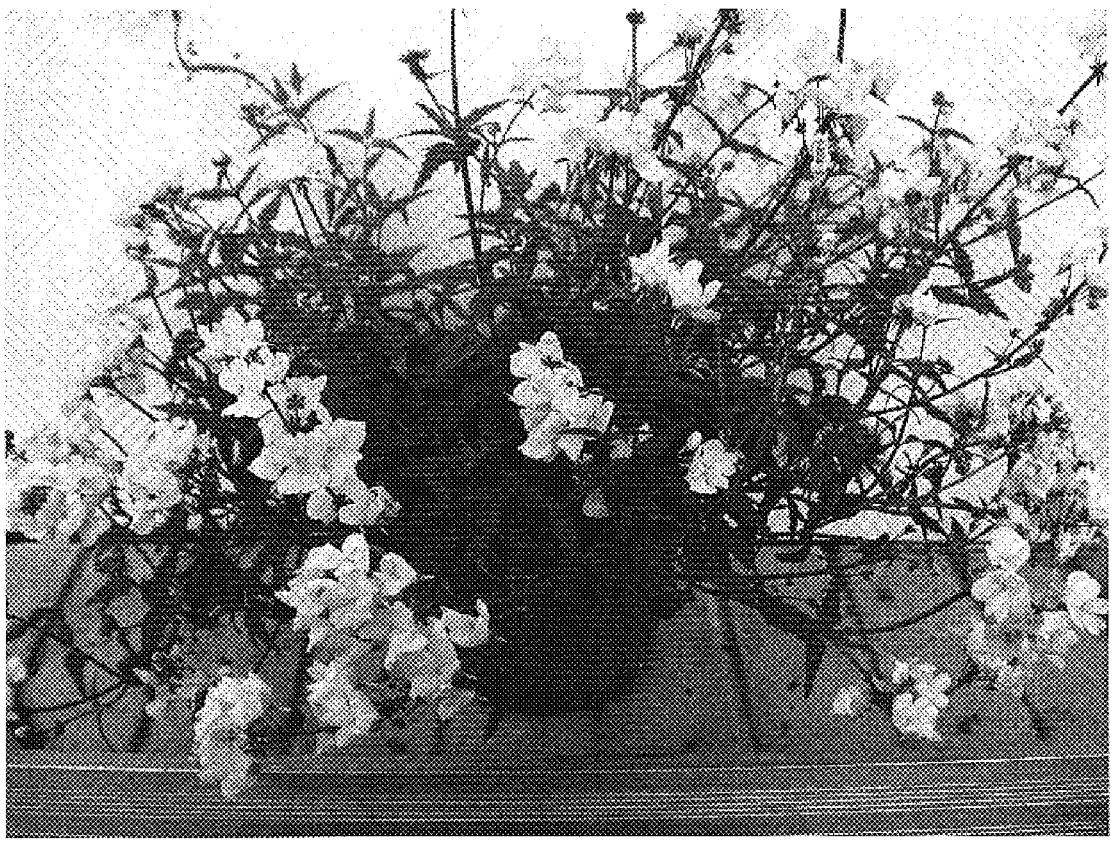

The accompanying photograph in FIG. 1 illustrates in full color a typical plant of 'Dannemes4' grown in a greenhouse, in a 16 cm pot. Age of the plant photographed is approximately 5 weeks from a rooted cutting, with 2 rooted cuttings planted in the pot shown.

Figure 2:
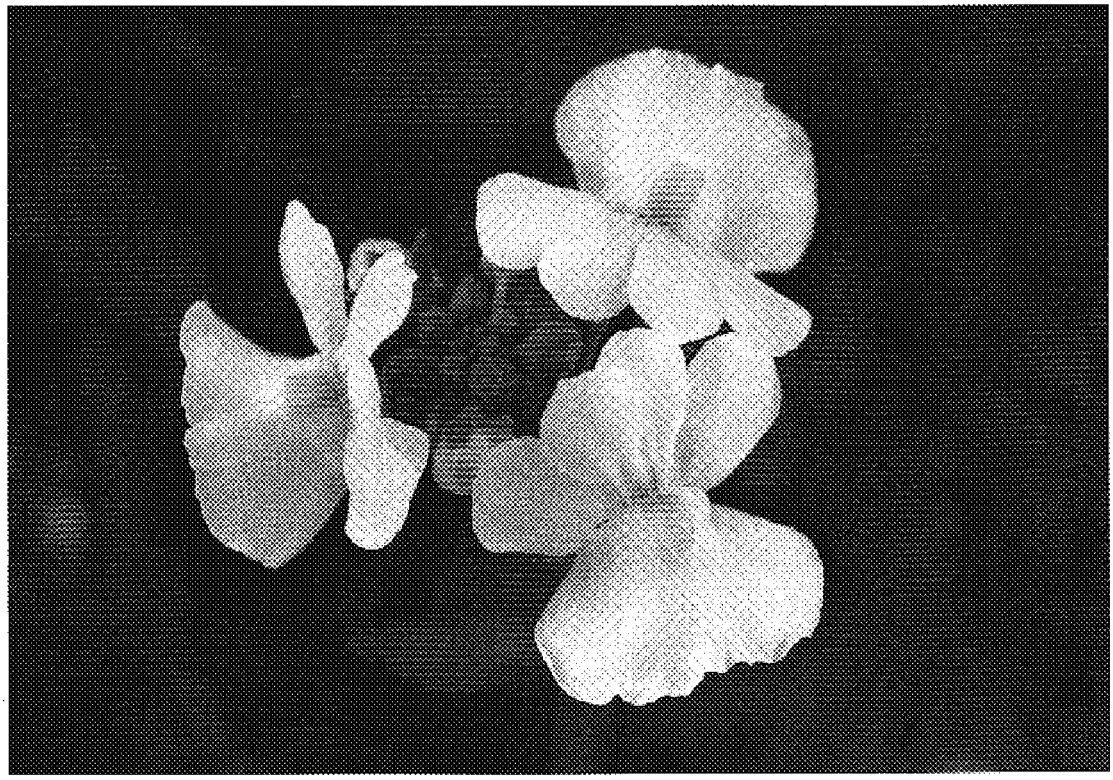

FIG. 2 illustrates in full color a close up of a typical bloom of 'Dannemes4.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart (2001 edition) and The Royal Horticultural Society Mini-Colour Chart (2005 edition) except where general terms of ordinary dictionary significance are used. The following observations and measurements describe 'Dannemes4' plants grown in a greenhouse in Moshav Mishmar Hashiva, Israel. The growing temperature ranged from 20° C. to 28° C. The greenhouse is un-shaded, giving bright, normal sunlight conditions. Measurements and numerical values represent averages of typical plant types.

Botanical classification: *Nemesia fruticans* cultivar 'Dannemes4.'

PROPAGATION

Time to initiate roots: About 5 days at approximately 15–25° C.
Time to develop roots: About 10 days at approximately 15–25° C.
Root description: Fine, densely fibrous.

PLANT

Growth habit: Upright.
Pot size of plant described: 12 cm.
Height:
*To top of flowers.*—Approximately 25–30 cm.
Plant spread: Approximately 20–25 cm.
Growth rate: Moderate.
Branching characteristics: Moderate branching.
Length of lateral branches: Approximately 25 cm.
Diameter of lateral branches: Approximately 0.2 cm.
Color of branches: Near RHS Yellow-Green 144A.
Texture: Glabrous.
Internode length: Approximately 3.5–4.0 cm.
Age of plant described: Approximately 63 days from a rooted cutting.

FOLIAGE

Arrangement: Opposite.
Leaves per branch: Approximately 8–10.
Leaves:
*Size.*—Length: About 3.5 cm. Width: About 1 cm. Shape of leaf: Oblong. Shape of apex: Acute. Shape of base: Acute. Texture: Glabrous. Aspect: Perpendicular to stem. Margin type: Serrate. Fragrance: Fragrant.
*Color.*—Young leaves: Upper surface: RHS Green 137B. Lower surface: RHS Green 138A. Mature leaves: Upper surface: RHS Green 137A. Lower surface: RHS Yellow-Green 146B.
Petiole:
*Length.*—Approximately 0.5–0.7 cm.
*Diameter.*—Approximately 0.2 cm.
*Color.*—Near RHS Green 143C.
Veins:
*Venation pattern.*—Pinnate.
*Color.*—Upper surface: RHS Yellow-Green 144A. Lower surface: RHS Green 143B.

FLOWER

Bud: Described 5 days before anthesis.
*Shape.*—Flattened oval.
*Diameter.*—Approximately 0.3–0.4 cm.
*Length.*—Approximately 0.4 cm.
*Color.*—Near RHS Yellow 1C.
Natural flowering season: Early spring, spring and autumn in Israel.
Flower type and habit: Zygomorphic.
Corolla:
*Upper petals* (*upper lip*).—Number: 4. Length: Central petals: 8–10 mm. Lateral petals: 8 mm. Width: Central petals: 6 mm. Lateral petals: 5 mm. Shape: Close to oblong. Aspect: 45 degrees to stem. Margin: Entire. Texture: Glabrous. Color: When opening: Upper surface: White N999D. Lower surface: White N999D. Fully opened: Upper surface: White N999D. Lower surface: White N999D.
*Lower petal* (*lower lip*).—Length: 1.5 cm. Width: 0.8 cm. Shape: Close to reniform. Apex shape: Blunt. Color: Upper surface: White N999D. Lower surface: White N999D.
*Palate.*—Length: 8 mm. Width: 5 mm. Color: Yellow 4B. Texture: Pubescent.
*Throat.*—Length: 6 mm. Width: 5 mm. Texture: Glabrous. Pubescence: None.
*Spur.*—Quantity: 1. Length: 4 mm. Diameter: 1 mm. Texture: Glabrous. Color: Yellow 4C.
Calyx:
*Form.*—5 none fused.
*Length.*—3 mm.
*Diameter.*—4 mm.
*Sepal.*—Width: 1 mm. Shape: Oblong. Apex: Acute. Margin: Entire. Texture: Puberulous. Color: Upper surface: Yellow-green 144A. Lower surface: Yellow-green 144A.
*Pedicel.*—Strength: Fragile. Aspect: Upright. Length: 8 mm. Diameter: 0.5 mm. Texture: Glabrous. Color: Yellow-Green 144A.
*Fragrance.*—Fragrant.

REPRODUCTIVE ORGANS

*Stamens.*—Number (per flower): 2. Filament length: About 0.3 cm. Anthers: Shape: Oval. Length: About 0.8 mm. Color: RHS Yellow 4B.
*Pollen.*—Color: RHS Yellow 4B. Amount: Abundant.
*Pistils.*—Quantity per flower: 1. Length: About 3.5 mm. Styles: Length: About 1.5 mm. Color: Yellow-Green 154A. Stigma: Shape: Oval. Color: Near RHS Yellow-Green 154A.

OTHER CHARACTERISTICS

Disease resistance: Neither resistance nor susceptibility observed.
Temperature tolerance: The new variety tolerates temperatures between 5 to 35° C.
Seed and fruit production: Produces large amounts of seed.

What is claimed is:

1. A new and distinct cultivar of *Nemesia* plant named 'Dannemes4' as herein illustrated and described.

* * * * *